(12) United States Patent
Byun et al.

(10) Patent No.: US 10,407,386 B2
(45) Date of Patent: Sep. 10, 2019

(54) METHOD FOR PREPARING D-ARGININE

(71) Applicant: AMINOLOGICS CO., LTD., Seoul (KR)

(72) Inventors: Il-Suk Byun, Seongnam-si (KR); Jung-Ho Lee, Incheon (KR); Hye-Lim Ga, Seoul (KR); Won-Sup Kim, Seongnam-si (KR)

(73) Assignee: AMINOLOGICS CO., LTD., Seoul (KR)

( * ) Notice: Subject to any disclaimer, the term of this patent is extended or adjusted under 35 U.S.C. 154(b) by 0 days.

(21) Appl. No.: 15/757,834

(22) PCT Filed: Sep. 6, 2016

(86) PCT No.: PCT/KR2016/009981
§ 371 (c)(1),
(2) Date: Mar. 6, 2018

(87) PCT Pub. No.: WO2017/043842
PCT Pub. Date: Mar. 16, 2017

(65) Prior Publication Data
US 2018/0354896 A1    Dec. 13, 2018

(30) Foreign Application Priority Data

Sep. 8, 2015 (KR) .................. 10-2015-0127203

(51) Int. Cl.
*C07C 277/08*   (2006.01)
*C07C 279/14*   (2006.01)

(52) U.S. Cl.
CPC ........ *C07C 277/08* (2013.01); *C07B 2200/07* (2013.01); *C07C 279/14* (2013.01)

(58) Field of Classification Search
None
See application file for complete search history.

(56) References Cited

U.S. PATENT DOCUMENTS

| 4,016,205 A | * | 4/1977 | Kariyone | ............... C07B 57/00 562/100 |
| 4,425,504 A | * | 1/1984 | Chibata | ................... G01J 5/34 250/338.3 |

(Continued)

FOREIGN PATENT DOCUMENTS

| CN | 102286602 A | 12/2011 |
| JP | H10-80297 A | 9/1996 |

(Continued)

OTHER PUBLICATIONS

Alfa Aesar Safety Data Sheet for D-3-bromocamphor-8-sulfonic acid, ammonium salt (https://www.alfa.com/en/content/msds/USA/A19886.pdf). (Year: 2012).*

(Continued)

*Primary Examiner* — Sudhakar Katakam
*Assistant Examiner* — Jennifer C Sawyer
(74) *Attorney, Agent, or Firm* — John P. White; Cooper & Dunham LLP

(57) ABSTRACT

This invention relates to a method of preparing D-arginine, and more particularly to a method of preparing D-arginine by optically resolving DL-arginine using D-3-bromocamphor-8-sulfonic acid or a salt thereof as an optical resolving agent.

5 Claims, 1 Drawing Sheet

(56) References Cited

U.S. PATENT DOCUMENTS

| | | | |
|---|---|---|---|
| 4,434,107 A * | 2/1984 | Chibata | C07C 227/34 |
| | | | 562/401 |
| 5,591,613 A | 1/1997 | Makryaleas | |

FOREIGN PATENT DOCUMENTS

| | | |
|---|---|---|
| JP | 2011-167107 A | 9/2011 |
| WO | WO 2016/028016 A1 | 2/2016 |

OTHER PUBLICATIONS

Sanford M. Birnbaum, et al., "Preparation of the Optical Isomers of Arginine, Histidine and S-Benzylcysteine by Asymmetric Enzymatic Hydrolysis of their Acetyl Derivatives" Archives of Biochemistry and Biophisics, 1952, National Cancer Institute, National Institutes of Health.

Sanford M. Birnbaum, et al., "A Simplified Preparation of D-Arginine" Archives of Biochemistry and Biophysics, Laboratory of Biochemistry, National Cancer Institute, National Institutes of Health, Bethesda, Maryland, 1956.

Yukiaki Nadai, "Studies on Arginase: I. Enzymatic Resolution of DL-Arginine into its Optical Antipodes", The Journal of Biochemistry, 1958, vol. 45, No. 9.

Clarence P. Berg, et at., "A simple method of preparing d-(–)-Arginine monohydrochloride from dl-arginine", Analytical Biochemistry, 1975.

International Search Report dated Dec. 19, 2016 in connection with PCT International Application No. PCT/KR2016/009981.

\* cited by examiner

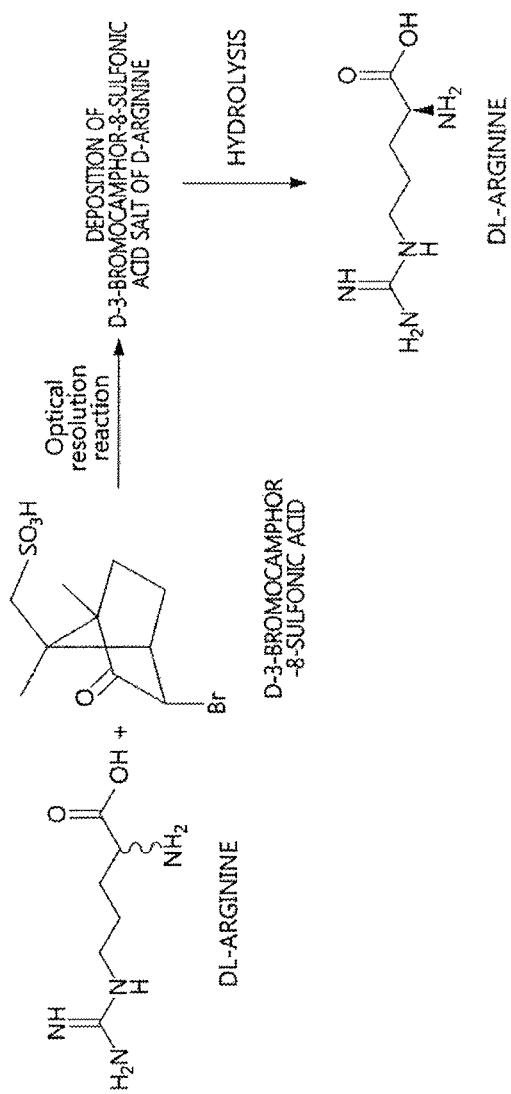

METHOD FOR PREPARING D-ARGININE

CROSS-REFERENCE TO RELATED APPLICATIONS

This application is a § 371 national stage of PCT International Application No. PCT/KR2016/009981, filed Sep. 6, 2016, claiming priority of Korean Patent Application No. KR 10-2015-0127203, filed Mar. 8, 2015, the contents of each of which are hereby incorporated by reference into the application.

TECHNICAL FIELD

The present invention relates to a method of preparing D-arginine, and more particularly to a method of preparing D-arginine in a manner in which DL-arginine is optically resolved using D-3-bromocamphor-8-sulfonic acid as an optical resolving agent and then hydrolyzed.

BACKGROUND ART

D-arginine is an ingredient that is essentially used in the production of medicaments such as desmopressin for the treatment of nocturnal enuresis, icatibant for the treatment of hereditary angioedema, and velcalcetide for the treatment of hyperparathyroidism.

Conventional techniques for preparing D-arginine may be largely classified into two types, one of which is a biological optical resolution reaction process using an enzyme, and the other of which is a chemical optical resolution reaction process using a chiral organic acid.

The preparation of D-arginine through a biological optical resolution reaction includes selectively obtaining D-acetyl-arginine from DL-acetyl-arginine through an optical resolution reaction using an enzyme and then hydrolyzing the D-acetyl-arginine, as is well known [Archives of Biochemistry Biophysics, 39, 108(1952); Archives of Biochemistry Biophysics, 60, 496(1956); The Journal of Biochemistry, 45(9), 687 (1958)], but is problematic because of the large number of processing steps and the requirement for the hydrolysis of D-acetyl-arginine, obtained through an optical resolution reaction, which is the key step, in a hydrochloric acid aqueous solution.

Furthermore, as an additional enzyme-assisted technique, U.S. Pat. No. 5,591,613 discloses a method of preparing D-arginine by selectively converting L-arginine of DL-arginine into L-ornithine using an enzyme, but is problematic because L-arginine contained in DL-arginine is not recovered but is decomposed.

On the other hand, the chemical optical resolution reaction using a chiral organic acid is advantageous in that chemical processing is easily performed using a simple apparatus compared to biological processing, and is thus suitable for mass production, but searching for and selecting chiral organic acids that serve as the optical resolving agent is regarded as very important, but is difficult.

In order to prepare D-arginine from DL-arginine, in Analytical Biochemistry, 63, 68(1975), it was reported that optical resolving agents such as tartaric acid, camphoric acid and glutamic acid have been utilized but failed to obtain desired results, and the separation of D-arginine using L-malic acid was also reported. To this end, however, complicated processing has to be performed in a manner in which a DL-arginine and L-malic acid aqueous solution is crystallized for one day in a refrigerator, thus obtaining primary crystals, which are then concentrated again to give secondary crystals. In particular, only the specific optical rotation ($[\alpha]_D$) of the obtained D-arginine is mentioned, and instrumental analysis by chiral chromatography has not been conducted, undesirably making it impossible to accurately confirm the optical purity of the obtained D-arginine.

DISCLOSURE

Technical Problem

Accordingly, the present invention has been made keeping in mind the problems encountered in the related art, and the present invention is intended to provide a method of preparing D-arginine by optically resolving DL-arginine using, as an optical resolving agent, D-3-bromocamphor-8-sulfonic acid or a salt thereof having an outstanding optical resolution effect among chiral organic acids.

Technical Solution

Therefore, the present invention provides a method of preparing D-arginine, comprising the steps of: (1) depositing a D-3-bromocamphor-8-sulfonic acid salt of D-arginine by optically resolving DL-arginine using, as an optical resolving agent, D-3-bromocamphor-8-sulfonic acid or a salt of D-3-bromocamphor-8-sulfonic acid and (2) hydrolyzing the deposited D-3-bromocamphor-8-sulfonic acid salt of D-arginine.

Advantageous Effects

According to the present invention, the method of preparing D-arginine is capable of preparing D-arginine by optically resolving DL-arginine using, as an optical resolving agent, D-3-bromocamphor-8-sulfonic acid or a salt thereof having an outstanding optical resolution effect, thereby increasing the optical purity of D-arginine and simplifying the processing steps, ultimately generating economic benefits and realizing the mass production of D-arginine.

Also, in the method of preparing D-arginine according to the present invention, a racemization catalyst is used together with the optical resolving agent, whereby an optical resolution reaction and a racemization reaction are carried out simultaneously, thus increasing the yield of D-arginine.

BRIEF DESCRIPTION OF DRAWING

FIG. 1 schematically shows the process of preparing D-arginine according to the present invention.

BEST MODE

Hereinafter, a detailed description will be given of the present invention.

In order to typically prepare D-arginine by chemically optically resolving DL-arginine, a chiral organic acid is used as an optical resolving agent, but searching for chiral organic acids suitable therefor remains very difficult. The chiral organic acids conventionally used are problematic because the preparation process of D-arginine is complicated and the optical purity thereof cannot be evaluated.

Hence, the present inventors have studied the optical resolution effects of DL-arginine using various kinds of chiral organic acids, and thus have ascertained that D-3-bromocamphor-8-sulfonic acid or a salt thereof may exhibit an outstanding optical resolution effect. Thus, in the present invention, D-arginine is prepared in a manner in which DL-arginine is optically resolved using D-3-bromocamphor-8-sulfonic acid or a salt thereof.

Specifically, the present invention addresses a method of preparing D-arginine by optically resolving DL-arginine using D-3-bromocamphor-8-sulfonic acid or a salt thereof as an optical resolving agent, and the D-arginine may be prepared through the following steps of:

(1) depositing a D-3-bromocamphor-8-sulfonic acid salt of D-arginine by optically resolving DL-arginine using, as an optical resolving agent, D-3-bromocamphor-8-sulfonic acid or a salt of D-3-bromocamphor-8-sulfonic acid; and (2) hydrolyzing the deposited D-3-bromocamphor-8-sulfonic acid salt of D-arginine.

In the step (1), D-3-bromocamphor-8-sulfonic acid has the structure of Chemical Formula 1 below.

[Chemical Formula 1]

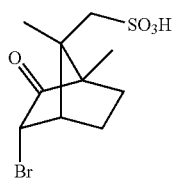

The D-3-bromocamphor-8-sulfonic acid or salt thereof is comprised in an amount of 0.5 to 1.5 equivalents, and preferably 0.5 to 1.1 equivalents, based on the amount of DL-arginine. If the amount of D-3-bromocamphor-8-sulfonic acid is less than 0.5 equivalents, optical resolution efficiency may decrease. On the other hand, if the amount thereof exceeds 1.5 equivalents, the yield of D-arginine may decrease.

Also, the kind of salt of D-3-bromocamphor-8-sulfonic acid is not particularly limited, but preferably includes D-3-bromocamphor-8-sulfonic acid ammonium salt.

DL-arginine is subjected to an optical resolution reaction using D-3-bromocamphor-8-sulfonic acid or a salt thereof as the optical resolving agent, whereby a D-3-bromocamphor-8-sulfonic acid salt of D-arginine is deposited in the form of a solid, and the deposited salt is obtained through filtration and then hydrolyzed, thus obtaining D-arginine.

In the step (1), when D-3-bromocamphor-8-sulfonic acid or a salt thereof, which is the optical resolving agent, is used alone, theoretically, D-arginine cannot be obtained at a yield of 50% or more. In order to overcome this problem, a racemization catalyst is further used, in addition to the optical resolving agent, whereby the optical resolution reaction and the racemization reaction are induced to occur at the same time, ultimately realizing a high yield of 50% or more. Furthermore, when the racemization catalyst is comprised, D-arginine may be prepared not only from DL-arginine but also from L-arginine.

The kind of racemization catalyst is not particularly limited, but preferably includes at least one selected from the group consisting of salicylaldehyde, 3,5-dichlorosalicylaldehyde and 5-nitrosalicylaldehyde, and more preferably includes salicylaldehyde.

The racemization catalyst is comprised in an amount of 0.05 to 0.2 equivalents based on the amount of DL-arginine. If the amount of the racemization catalyst is less than 0.05 equivalents, racemization efficiency may decrease. On the other hand, if the amount thereof exceeds 0.2 equivalents, the yield of the resulting salt is low.

The step (2) is obtaining D-arginine by hydrolyzing the D-3-bromocamphor-8-sulfonic acid salt of D-arginine deposited in the step (1).

The hydrolyzing step may be performed using typically known various processes, and preferably using an ion exchange resin.

When an ion exchange resin is used, the D-3-bromocamphor-8-sulfonic acid salt of D-arginine, deposited in the form of a solid in the step (1), is dissolved in water, after which the salt is subjected to a typical ion exchange resin process including adsorption to an ion exchange resin, desorption using an ammonia aqueous solution and then concentration, thereby yielding D-arginine.

The optical purity of the D-arginine thus prepared may be analyzed using a chiral column.

A better understanding of the present invention may be obtained via the following examples, which are merely set forth to illustrate but are not to be construed as limiting the scope of the present invention.

MODE FOR INVENTION

Preparation of D-Arginine

Example 1

200 mL of methanol and 80 mL of acetic acid were added with DL-arginine (10 g, 57.4 mmol) and D-3-bromocamphor-8-sulfonic acid ammonium salt (18.8 g, 57.4 mmol), heated to 50° C. to thus be dissolved, and then slowly cooled.

The resulting solution was stirred at 5° C. for 3 hr, and the deposited D-3-bromocamphor-8-sulfonic acid salt of D-arginine was obtained through filtration.

Thereafter, the salt was dissolved in distilled water and passed through a column packed with an ion exchange resin (IRC-86, $NH_4$ type) to adsorb D-arginine, after which the adsorbed D-arginine was desorbed using 5% ammonia water, and the resulting desorbed aqueous solution was concentrated again, thus yielding D-arginine.

The optical purity of the D-arginine thus obtained was analyzed using a chiral column (Sumichiral OA-5000 column). The analysis conditions were as follows.

Column: Crownpak CR(+)

Mobile phase: Perchloric acid aqueous solution ($HClO_4$) at a pH of 1.5

Detector: UV (200 nm)

Based on the analysis results of the optical purity of D-arginine under the above analysis conditions, 2.9 g of the obtained D-arginine was found to include D-arginine and L-arginine at a ratio of 96:4.

Example 2

400 mL of propionic acid was added with DL-arginine (20 g), D-3-bromocamphor-8-sulfonic acid ammonium salt (39.6 g) and salicylaldehyde (1.1 g) and then heated to 60° C.

The resulting solution was stirred at 60° C. for 25 hr and cooled to room temperature, after which the deposited D-3-bromocamphor-8-sulfonic acid salt of D-arginine was obtained through filtration.

Thereafter, the salt was dissolved in distilled water and passed through a column packed with an ion exchange resin (IRC-86, $NH_4$ type) to adsorb D-arginine, after which the adsorbed D-arginine was desorbed using 5% ammonia water, and the resulting desorbed aqueous solution was concentrated, thus yielding D-arginine.

The optical purity of D-arginine thus obtained was analyzed using a chiral column (Sumichiral OA-5000 column) under the same conditions as in Example 1.

Based on the analysis results of the optical purity of D-arginine under the above analysis conditions, 15.7 g of the obtained D-arginine was found to include D-arginine and L-arginine at a ratio of 98:2.

Example 3

1000 mL of propionic acid was added with L-arginine (50 g), D-3-bromocamphor-8-sulfonic acid ammonium salt (94.2 g) and salicylaldehyde (1.7 g) and then heated to 65° C.

The resulting solution was stirred at 65° C. for 20 hr and cooled to room temperature, after which the deposited D-3-bromocamphor-8-sulfonic acid salt of D-arginine was obtained through filtration.

Thereafter, the salt was dissolved in distilled water and passed through a column packed with an ion exchange resin (IRC-86, $NH_4$ type) to adsorb D-arginine, after which the adsorbed D-arginine was desorbed using 5% ammonia water and the resulting desorbed aqueous solution was concentrated, thus yielding D-arginine.

The optical purity of the D-arginine thus obtained was analyzed using a chiral column (Sumichiral OA-5000 column) under the same conditions as in Example 1.

Based on the analysis results of the optical purity of D-arginine under the above analysis conditions, 38.2 g of the obtained D-arginine was found to include D-arginine and L-arginine at a ratio of 97:3.

Based on the results of Examples 1 to 3, the method of preparing D-arginine according to the present invention can be concluded to exhibit high yield and a simple preparation process and to be effective for the mass production of D-arginine.

Also, when an optical resolving agent, such as D-3-bromocamphor-8-sulfonic acid or a salt thereof, and a racemization catalyst are used together, an optical resolution reaction and a racemization reaction can be simultaneously carried out, thereby obtaining D-arginine at a higher yield.

The invention claimed is:

1. A method of preparing D-arginine, comprising the steps of:
   (1) depositing a D-3-bromocamphor-8-sulfonic acid salt of D-arginine by optically resolving DL-arginine using, as an optical resolving agent, D-3-bromocamphor-8-sulfonic acid or a salt of D-3-bromocamphor-8-sulfonic acid; and
   (2) hydrolyzing the deposited D-3-bromocamphor-8-sulfonic acid salt of D-arginine,
   wherein the D-3-bromocamphor-8-sulfonic acid or the salt of D-3-bromocamphor-8-sulfonic acid is comprised in an amount of 0.5 to 1.5 equivalents based on an amount of DL-arginine, and
   wherein in the step (1), a racemization catalyst is further used so that a racemization reaction and an optical resolution reaction are simultaneously carried out.

2. The method of claim 1, wherein the salt of D-3-bromocamphor-8-sulfonic acid includes a D-3-bromocamphor-8-sulfonic acid ammonium salt.

3. The method of claim 1, wherein the racemization catalyst includes at least one selected from the group consisting of salicylaldehyde, 3,5-dichlorosalicylaldehyde and 5-nitrosalicylaldehyde.

4. The method of claim 3, wherein the racemization catalyst is comprised in an amount of 0.05 to 0.2 equivalents based on an amount of DL-arginine.

5. The method of claim 1, wherein the hydrolyzing in the step (2) is performed using an ion exchange resin.

* * * * *